(12) United States Patent
Ruetenik

(10) Patent No.: US 11,766,320 B2
(45) Date of Patent: Sep. 26, 2023

(54) EQUINE IMAGING SAFETY RESTRAINT AND POSITIONING

(71) Applicant: Monty L. Ruetenik, Clear Lake Shores, TX (US)

(72) Inventor: Monty L. Ruetenik, Clear Lake Shores, TX (US)

(73) Assignee: MONTY L. RUETENIK, Clear Lake Shores, TX (US)

(*) Notice: Subject to any disclaimer, the term of this patent is extended or adjusted under 35 U.S.C. 154(b) by 277 days.

(21) Appl. No.: 16/839,313

(22) Filed: Apr. 3, 2020

(65) Prior Publication Data

US 2020/0330207 A1 Oct. 22, 2020

Related U.S. Application Data

(60) Provisional application No. 62/836,074, filed on Apr. 19, 2019.

(51) Int. Cl.
*A61D 3/00* (2006.01)
*A61B 6/00* (2006.01)
*A61B 6/04* (2006.01)
*A61B 8/00* (2006.01)
*A61B 5/055* (2006.01)

(52) U.S. Cl.
CPC .......... *A61D 3/00* (2013.01); *A61B 5/055* (2013.01); *A61B 6/04* (2013.01); *A61B 6/508* (2013.01); *A61B 8/40* (2013.01); *A61B 2503/40* (2013.01); *A61D 2003/006* (2013.01)

(58) Field of Classification Search
CPC ...... A61D 3/00; A61D 2003/006; A61B 6/04; A61B 6/0407; A61B 6/0421; A61B 6/0428; A01K 13/007; A01L 7/00; A01L 7/02

USPC .................................. 54/82; 168/4; 600/407
See application file for complete search history.

(56) References Cited

U.S. PATENT DOCUMENTS

| | | | | |
|---|---|---|---|---|
| 6,443,231 B1* | 9/2002 | Edwards | ............... | A01L 11/00 168/1 |
| 8,656,691 B2* | 2/2014 | Ruetenik | ............... | A01L 15/00 168/28 |
| 10,136,870 B2* | 11/2018 | Ray | ............... | A61B 6/032 |
| 10,136,871 B2* | 11/2018 | Yorkston | ............... | A61B 6/4452 |
| 10,375,946 B2* | 8/2019 | Ruetenik | ............... | A01L 15/00 |
| 2003/0070403 A1* | 4/2003 | Osha | ............... | A01L 15/00 54/82 |
| 2014/0033661 A1* | 2/2014 | Ruetenik | ............... | B29C 39/02 168/28 |
| 2016/0361036 A1* | 12/2016 | Ray | ............... | A61B 6/508 |

FOREIGN PATENT DOCUMENTS

WO WO-2015054466 A1 * 4/2015 ............. A61B 6/032

* cited by examiner

*Primary Examiner* — Peter M Poon
*Assistant Examiner* — Danielle A Clerkley
(74) *Attorney, Agent, or Firm* — Boulware & Valoir, PLLC

(57) ABSTRACT

A system for use in positioning and restraining an equine hoof during imaging, with at least one panic-releasable connection. The system may comprise an equine boot and an interface plate attached to the underside thereof, a receiver plate attached to a limb placement region of an imaging apparatus, and a placement plate attached to the receiver plate. Further disclosed is use of one or more components apart from the whole system, and methods of use for positioning and restraining an equine hoof during imaging.

9 Claims, 6 Drawing Sheets

EQUINE IMAGING SAFETY RESTRAINT AND POSITIONING

PRIOR RELATED APPLICATIONS

This application claims priority to U.S. Ser. No. 63/836,074, filed Apr. 19, 2019, incorporated by reference in its entirety for all purposes.

FEDERALLY SPONSORED RESEARCH STATEMENT

Not applicable.

FIELD OF THE INVENTION

This invention relates to equine imaging. In particular, it relates to safety restraint and positioning for equine limbs during standing imaging procedures.

BACKGROUND OF THE DISCLOSURE

Various imaging techniques are available m equine veterinary medicine to enable visualization of various body structures and aid in localization and diagnosis of various abnormalities and diseases. Imaging techniques include radiography (X-ray), ultrasound (US), nuclear scintigraphy (NS), magnetic resonance (MR), or magnetic resonance imaging (MRI). Aspects of NS are described in "Nuclear Scintigraphy in Horses" [1], which is incorporated herein by reference. Aspects and benefits of MRI are described in "Equine MRI" [2], "Standing Magnetic Resonance Imaging [3], and Magnetic Resonance Imaging of the Distal Limb of the Standing Horse [4], which are all incorporated herein by reference.

One of the difficulties of many imaging techniques is the requirement for the equine to remain still during the imaging procedure. MR, in particular, is a longer process than, for example, a single X-ray, and the imaging quality is often very sensitive to motion.

In order to achieve the minimal to no motion required to obtain quality images, imaging clinics typically sedate the equines being imaged. Some imaging systems provide motion stabilization software to help reduce image artifacts due to minimal animal motion during the imaging process, but light sedation is still required.

Standing imaging techniques, such as standing NS and standing MRI, are growing in popularity due to decreased costs and health risk associated with avoiding full anesthesia of the animal, and increasing safety for veterinary personnel by avoiding the risks of anesthesia and positioning on a table. While light sedation can be used with at least some standing imaging techniques, there is still a need for a means and method of positioning the equine limb for imaging and restraining it during the imaging process. It is of paramount importance that equine and human safety be preserved during restraint and positioning.

The present invention provides a means and method suitable, in various embodiments encompassed herein, for equine limb positioning, restraint, or both during imaging, and provides means and methods for preserving human and equine safety.

SUMMARY OF INVENTION

A system for use in positioning and restraining an equine hoof during imaging, the system being panic-releasable. The system comprises an equine boot and an interface plate attached to the underside thereof, a receiver plate attached to a limb placement region of an imaging apparatus, and a placement plate attached to the receiver plate. The invention also encompasses various structures of the system and methods of using the structures individually and the system as a whole in positioning and restraining equines during imaging.

DESCRIPTION OF THE DRAWINGS

Various embodiments of the present embodiments are described with reference to the following FIGURES. Like reference numerals therein refer to like parts throughout the various views unless otherwise specified. Embodiments and portions of embodiments illustrated and described herein are non-limiting and non-exhaustive.

DETAILED DESCRIPTION OF THE INVENTION

Figure 1:
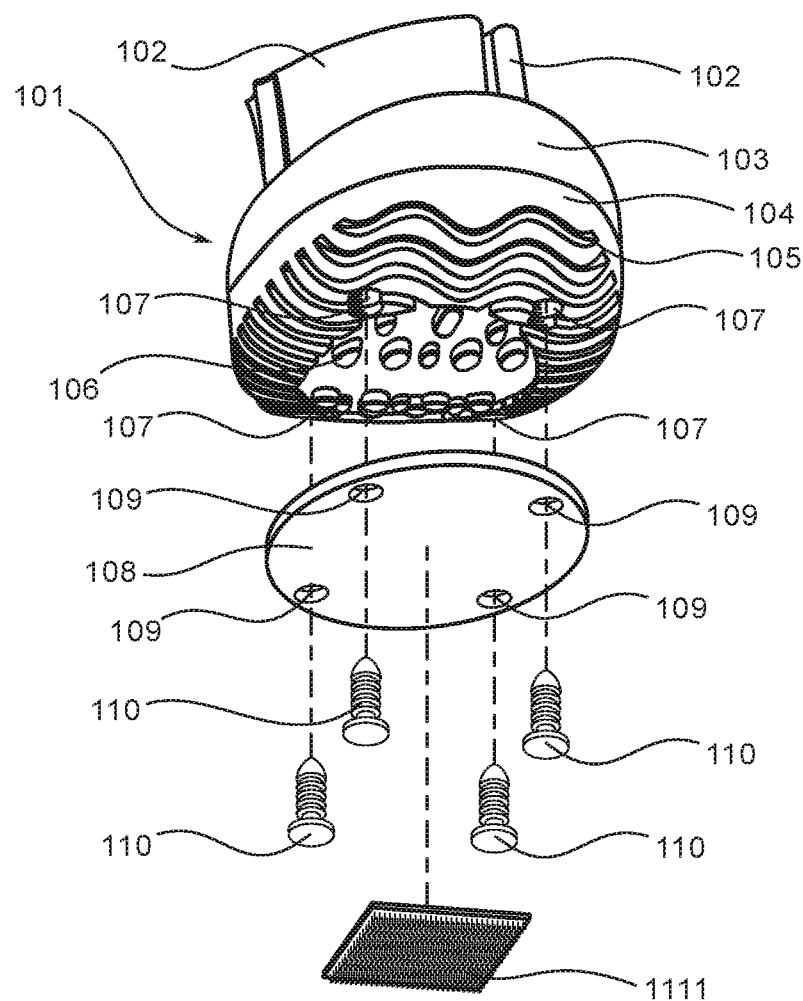
FIG. 1 is a perspective exploded assembly view of at least some portion of an embodiment of the invention comprising a boot, interface plate, hook-and-loop material, and rivets.
Figure 2:
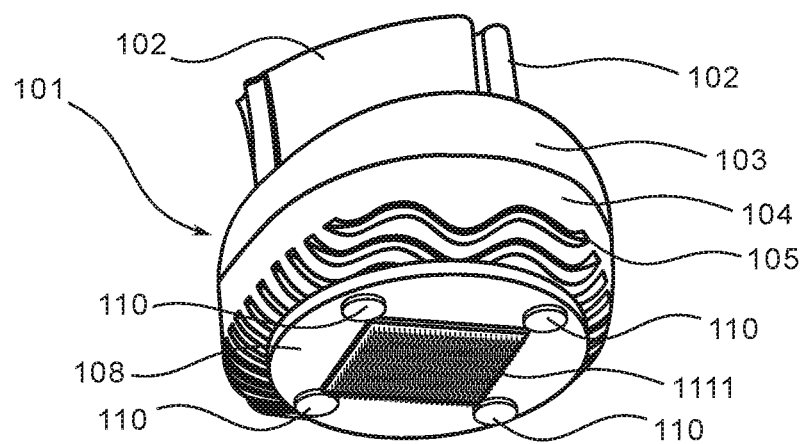
FIG. 2 is a perspective assembled view of FIG. 1.

The following description of various embodiments of the invention, combined with the associated drawings, enables persons of ordinary skill in the art to both practice the preferred embodiments of the invention, and to understand related applications and embodiments of the invention that may not be specifically set forth, but are encompassed by the specification and claims.

GENERAL EMBODIMENT

Embodiments disclosed herein relate to a system for use in positioning and restraining an equine hoof during imaging, the system being panic-releasable. The system comprises an equine boot and an interface plate attached to the underside thereof, a receiver plate attached to a limb placement region of an imaging apparatus, and a placement plate attached to the receiver plate. In some embodiments, the interface plate is multi-strata.

In preferred embodiments, the interface plate and placement plate are each provided with an attachment mechanism. The attachment mechanisms of the interface plate and the placement plate mate together to releasably and panic-releasably secure the interface plate and placement plate together such that the attachment is at least released when the interface plate is separated from the placement plate, for example by initiating a peeling motion of the interface plate with at least a pre-determined release-activation force.

In preferred embodiments, there are at least five panic-releasable attachments:
1. The releasable attachment of the boot onto the equine.
2. The attachment of the boot to the interface plate.
3. The attachment of the interface plate to the placement plate (such as previously described).
4. The attachment of the placement plate to the receiving plate.
5. The attachment of the receiving plate to the imaging apparatus/limb-placement region.

In preferred embodiments, the panic-releasable attachment between the interface plate and the placement plate requires the least force to release of the panic-releasable attachments. In preferred embodiments, the panic-releasable attachment between the placement plate and the receiver plate, and, when secured, the attachment between the receiver plate and the imaging apparatus or limb-placement region, both require greater force to release than any other of the panic-releasable attachments.

Various embodiments also include one or more of the components discussed herein.

Further embodiments include methods of using various components disclosed herein, combinations thereof, or the system as a whole for positioning and restraining equines during imaging.

Various combinations of the different elements of embodiments of the invention as herein defined will be obvious to those in the art as appropriate for the specific application and environment of use, as set forth herein.

Panic Releasable

As used herein, panic-releasable means that the attachment or connection is intended to remain in place during normal use. In the case of an animal panicking, however, the attachment is designed to separate to allow the equine to free itself without further damage. This is a critical point, as animals in general, and equines in particular, can become frightened in unfamiliar surroundings and procedures, and can begin frantic attempts to free themselves. If restraining structures are not designed with the strength, stability, and safety features to fully restrain the panicked equine, the equine can seriously injure itself—such as broken limbs, pulled tendons or ligaments, or worse. Further, the equine, in its attempts to free itself, can thrash about and injure personnel, bystanders, etc.

For example, if an equine hoof was strapped into place during imaging, and the equine became panicked and began trying to free itself, but the strapping held firm even though it is not designed to totally restrain the equine, the equine could easily lose balance and fall over. In that case, the likelihood of the equine breaking a limb, striking its head, and even killing itself is high. Also high is the likelihood of the equine striking out with its feet while thrashing and even accidentally injuring or killing a human, falling on and crushing a human, falling on a structure and knocking it over, breaking a container or piping and releasing a potentially harmful or dangerous substance, other catastrophic consequences, or combinations thereof.

If the attachment is designed to be panic-releasable, however, it is designed to strategically fail to preserve safety. In the same circumstance as above, it will hold the equine restrained during normal use. However, if the equine becomes panicked and begins struggling to be released, at least one of the panic-releasable connections will designedly fail, and the equine will be able to free its foot. Typically, once an equine feels itself no longer bound to the perceived source of danger or concern, it will calm, or at least allow itself to be calmed. At the very least, it will no longer feel the need to thrash about and free itself from the attachment that is now broken.

As used herein, panic-releasable is distinct from releasable. A panic-releasable attachment is not necessarily intended to be released under normal circumstances, or under the circumstances in which it would be released during panic. On the other hand, a releasable attachment is intended to be released, at least under a given set of circumstances. In other words, a panic-releasable attachment infers that the attachment is designed to potentially release in event of the equine panicking, without necessarily requiring intervention by a person. A releasable attachment infers that the attachment is designed to be released under normal circumstances, typically by a person.

For example, in various embodiments of the present invention, a hook-and-loop attachment is made between the interface plate and the placement plate. This is both a releasable and a panic-releasable connection. It is intended to be releasable under normal use (for example, by initiating a peeling motion to release the hook-and-loop connection). It is also releasable during panic for safety reasons: if an equine panics, it can inadvertently 'peel' itself free while struggling, and can even, with enough effort, simply snatch the hook-and-loop connection apart.

In another example, in various embodiments of the present invention, the connection between the interface plate and the boot is panic-releasable, but not necessarily releasable (although it may be in some embodiments and in many embodiments it is separable with some effort and possible destruction of the attachment means). The interface plate in some such embodiments is plastic-riveted (such as with fir-tree style rivets) to the bottom of the boot. The plastic rivets are not inherently releasable—they are intended under normal circumstances to hold the interface plate to the boot during positioning and re-positioning which, in some embodiments, involves connecting and separating hook-and-loop fabric between the interface plate and the placement plate. However, they are panic-releasable because, during panic, the equine is capable of breaking or pulling free the plastic rivets to release its hoof. Although the hook-and-loop connection between the interface plate and placement plate should release first, if that safety release fails (and potentially other safety release points), the plastic rivets can be broken during the exertions of a panicked horse, thereby releasing the equine's hoof and at least partially eliminating the cause for panic.

Major Components

In various preferred embodiments, the system disclosed herein comprises five major components: the boot, the interface plate, the placement plate, the receiving plate, and the imaging apparatus.

The Boot

In various embodiments, the boot functions as a restraint and protective structure, which is secured to the equine hoof and which—often through intermediary structures—attaches to a placement pad, thereby allowing personnel to restrain the booted hoof in a desired position for imaging (or another suitable procedure). The boot acts as a protective structure by at least partially surrounding the hoof and, in some embodiments, cushioning it.

In some embodiments, the boot may be replaced with a shoe, collar, harness, garter, or other suitable restraint attachment structure. In some embodiments encompassed herein, such as those in which a body part other than a hoof is being positioned (such as the head, neck, leg, or other desired body part), those in which an animal other than an equine is being positioned (such as bovines, ovines, caprines, porcines, canines, felines, camelids, avians, etc.), or combinations thereof, the boot may be a suitable restraint attachment structure, such as a band, a halter, a headstall, a helmet, a hood, jacket, a bag, etc. In some embodiments with a shoe or similar structure, the shoe may be attached by nails, adhesive, or other suitable mechanisms.

In preferred embodiments, such as those shown in FIGS. 1-6, the equine boot is an equine boot assembly having a slightly flexible, yet relatively rigid sole (104, 604), a flexible fabric upper (103, 603) with hook-and-loop closures (102, 602), and an elastomeric gel orthotic pad (not shown) disposed within the boot on which the equine hoof (127) stands. The hook-and-loop closures close a padded collar (119) around the equine leg, thereby securing the boot onto the hoof. Suitable such boot assemblies and related components are described in the following patent publications, the disclosures of which are incorporated herein by reference: U.S. Pat. No. 8,291,683 (issued Oct. 23, 2012), US20170280682A1 (published Oct. 5, 2017), US20170099825A1 (published Apr. 13, 2017), US20140033661A1 (published Feb. 6, 2014), USD616614S1 (issued May 25, 2010), U.S. Pat. No. 8,220, 231B2 (issued Jul. 17, 2012), and U.S. Pat. No. 7,445,051B2 (issued Nov. 4, 2008).

The boot must be procedure suitable. In preferred embodiments, the procedure is imaging, include imaging modalities such as magnetic resonance imaging (MRI), nuclear scintigraphy (NS), radiography (X-Ray), computed tomography (CT) or computed axial tomography (referred to herein also as CT), Ultrasound (US), or other imaging procedures. The system may also be advantageously used for positioning for visual examination, physical examination, injections, diagnosis, therapy, etc.—most situations in where a firm but safe localized restraint is desired.

In embodiments optimized for various imaging modalities, the boot is suitable for the imaging modality. For example, boots in various MRI-optimized embodiments have little or, preferably, no ferrous metal, which can not only interfere with imaging but may pose a safety hazard when exposed to a strong magnetic field by pulling the ferrous metal strongly—even violently—toward the source of the magnetic field, and potentially injuring any attached or interfering body part in the process.

In various x-ray-optimized embodiments, the boot is of relatively low radiopacity, such as by eliminating metal and other materials of high radiopacity. Similar embodiments are also suited for CT and NS, although NS has relatively lower signal strength and so will be more sensitive to radiopaque materials and, therefore, requires further optimization reducing radiopacity of the boot in some embodiments (for example, as by a sandal and leg harness, or a boot with openings). In various US-optimized embodiments, the boot is configured to permit direct access to the portion of the hoof of interest to eliminate boot material between the US—transducer and the hoof. Such configuration may include flaps (which, in some embodiments, are fastened and released by hook-and-loop closures, snaps, hooks, straps, buttons, zippers, etc.), openings, cutaways, etc.

Some similar embodiments position and restrain the hoof or other body portion while providing access for surgery, injection, biopsy, examination, etc. For example, in embodiments for surgery under full anesthetization, a hoof is be placed in a boot and positioned and restrained in a particular location to provide greater stability and maintain optimal positioning for the surgeon to enable more precise and rapid completion of the surgical procedure. Other such embodiments are adapted for procedures on the head by providing a halter, headstall, hood, or similar structure that is positioned on a surgery table (or other procedure-suitable placement plate) to position and restrain the head. Other such embodiments are adapted for procedures on a limb, by providing at least one garter on at least one leg and positioning and restraining the leg on a surgery table (or other procedure-suitable placement plate). Other such embodiments are encompassed herein.

Other similar embodiments are adapted to other imaging modalities, such as a lead-lined boot with an aperture to allow x-rays (or other electromagnetic waves) to pass through to the hoof. Similar such embodiments are adapted to treatments, such as confocal radiation therapy, such as for treatment of cancer, allowing concentration of the radiation on a specific body portion, while shielding surrounding tissue from the radiation. Similar embodiments are adapted to other portions of the body for similar methods and modes of action, according to the disclosure herein.

The Interface Plate

The interface plate (which may also be referred to as an "interface pad") provides an interface between the placement pad and the boot. The interface plate is attached to the hoot, and is provided with a releasable means of attaching to the placement pad. In various preferred embodiments, one side of a hook-and-loop material is secured to the interface plate. For example, in some such embodiments, shown in FIGS. 1-6, the interface plate (108, 608) is an elastomer (with polyurethane being advantageously used in some embodiments) formed by casting in a mold, and the hook or loop material (1112, 6112) is embedded in the interface plate before the elastomer cures. The hook or loop portion of the hook or loop material embedded in the elastomer is left free and unfilled with elastomer, while the backing portion of the material (often a woven fabric), is embedded in the elastomer before curing. Once the elastomer cures, the hook or loop material is thereby strongly attached to the interface plate, and provides the interface plate with a means of attaching to the placement pad (112, 612). A suitable process for attaching hook-and-loop material to a polyurethane structure is disclosed in US2017/0290317A1 (published Oct. 12, 2017), the disclosure of which is incorporated by reference. The process disclosed is optimized for use with dispersed particles, such as is disclosed herein. In some embodiments herein, the process is used without dispersed particles: a double-sided Velcro®—type hook-and-loop tape is secured to the bottom of the pad or plate, by embedding one side of the tape in the uncured elastomer comprising at least the outermost stratum of the pad or plate, while leaving the other side of the tape free from the elastomer. As the elastomer cures, the hook-and-loop tape is embedded securely in the pad or plate by one side, and the other side of the tape can be used to form an attachment to another structure via a mating hook-and-loop material.

A similar method is used, as applicable, for some embodiments of other plates and pads herein (such as the receiving plate). In other embodiments, the hook-and-loop material is sewn to the pad or plate by a heavy sewing machine.

The interface plate is secured to the boot by a suitable attachment mechanism. In preferred embodiments, the attachment is panic-releasable. In some such embodiments, the interface plate is attached to the underside of the boot by one or more plastic rivets. Fir-tree style rivets, or ratcheting rivets, may be advantageously used. In some such preferred embodiments, such as those shown in FIGS. 1, 2, 3, and 7, four fir-tree style rivets (110, 610) are provided around the perimeter of the interface plate. In the illustrated embodiments, matching holes (107) are provided, either during manufacture or field-added, in the base plate of the boot. The rivets may then be pushed through holes (109, 609) in the interface plate, and into the holes in the base plate of the boot, thereby securing the interface plate to the underside of the boot.

In some such embodiments, and similar embodiments, the holes are provided such that the interface plate is automatically fixed in a desired orientation. The interface plate is also provided, in some embodiments, with a three dimensional profile on the upper surface that at least partially mates with that of the underside of the boot, provided advantages such as improved force transfer directly between the base plate and the boot, improved rotational stability between the hoof and interface plate, improved shear resistance between the hoof and interface plate, and proper alignment of attachment mechanisms between the interface plate and the placement pad.

In some embodiments, the holes are counterbored such that the rivet heads are recessed flush with or sub-flush with the interface plate. In some such embodiments, the hook-and-loop material thus stands proud of the interface plate, maximizing connection with the hook-and-loop material of the placement plate.

In some embodiments, the interface plate is a multi-strata pad. In some such preferred embodiments, an upper stratum is made of a softer material, and a lower stratum is made of a harder material. For example, such an interface plate, one stratum is made of polyurethane and is poured in an open mold, and a second stratum is also made of polyurethane poured on top of it to form a unitary structure with strong attachment between the strata (by being cast onto one another), while preserving the advantage of two different materials. The softer, upper strata 'nestles' into the boot, providing advantageous mechanical joining, shock absorption, and minor movement dampening, while the harder lower strata provides adequate support and rigidity to allow the interface plate and placement plate to connect and release properly. Too soft an interface plate (at least at the lowermost stratum) can allow, for example, embedded hook-and-loop tape to 'ripple' with movement that causes flexing of soft material, thereby inadvertently releasing the connection between the interface plate and placement plate when not expected. Too soft a lowermost stratum also can allow the embedded hook-and-loop tape to flex and remain connected during a 'peeling' motion while attempting to roll the boot forward and release the boot, thereby making it unnecessarily difficult. A certain degree of elasticity, however, is desirable in some embodiments in at least the lowermost stratum (in a multi-strata configuration, or in the entire pad in a single-stratum configuration) to which the embedded hook-and-loop tape is attached, thereby allowing the hook-and-loop tape to remain connected despite minor geometry mismatches between the placement plate and interface plate. Similarly, a certain degree of elasticity is desirable in at least the uppermost stratum (in a multi-strata configuration, or in the entire plate in a single-stratum configuration) of the placement plate, thereby allowing the placement plate and interface plate to conform to one another and create a secure connection therein between, while still remaining reasonably releasable and panic-releasable and avoiding the difficulties discussed above with too compliant ('soft') a material.

In various embodiments, other attachment mechanisms are used additionally or alternatively, such as bolts and nuts, adhesive, snaps, twist-lock fasteners, an interlocking system whereby bosses and recesses snap or twist-lock together, or some combination thereof. In some embodiments, a combination of rivets and other attachment mechanisms, such as interlocking geometry, is used. In some embodiments, the interface plate is integrated into the underside of the boot, thereby forming a single structure or assembly with the base plate of the boot.

In some embodiments, the boot is an equine shoe. In some such embodiments, the equine shoe is a multi-strata shoe, sandal, assembly of leg harness and rocker, or similar structure, such as those described in publication US2017/0172134A1(pub134), published Jun. 22, 2017, and in publication US2017/0027150A1 (pub150), published Feb. 2, 2017, both of which are incorporated herein by reference for all purposes.

In some such embodiments, the interface plate is attached to the underside of the shoe, as described in regards to a boot and interface plate elsewhere herein, such as by holes (manufacturer- or field-provided) and rivets.

In other such embodiments, the interface plate is integrated into the shoe to form a single structure. In some such embodiments, the attachment mechanism of the integrated interface plate is hook or loop material (such as is discussed elsewhere herein in regards to a boot and interface plate) embedded in the underside of the shoe, suitable for connection with the placement plate, as discussed elsewhere herein. Some such embodiments provide an advantage of being able to be attached by a hook-and-loop harness, such as is referenced in pub134, attached by wrapping at least part of each of the hoof and shoe with casting tape, elastic tape (such as 3M VetWrap), or other similar means or combinations of means, such as those disclosed in the referenced publications.

In some embodiments, the interface plate attaches to the placement plate by 'gecko-type' adhesion (such as through large surface area and Van der Waals forces, as discussed in "Gecko feet," [5] incorporated herein by reference). In some embodiments, the interface plate attaches to the placement plate by magnetic force, including through electromagnets positioned in the interface plate, the placement plate, or both, and attracted to a magnetic material, a complementary magnetic field, or some combination thereof. Some such embodiments have a switch or other means of activating or deactivating the electromagnetics for ease of use, positioning and repositioning, and safety. In some such embodiments, a sensor system disables the electromagnetics when indicators of panic are detected. In some magnetic embodiments, permanent magnets are used, and provided with a means of physically distancing the magnets from the opposite structure, such as a lever that lifts the magnets away from the surface so that the magnetic force is reduced and thereby allowing the hoof to be moved or removed.

In some embodiments with boots, and similar embodiments, the interface plate is not attached to the underside, or not attached solely to the underside of the boot but to the side, rear, front, top, or some combination thereof. Such embodiments are useful, for example, in combination with some NS procedures in which an upper portion of the hoof or of the leg is being acquired, and the hoof, leg, or both needs to be secured against a vertical surface.

The Placement Plate

The placement plate (which may also be referred to as a positioning plate, positioning pad, or placement pad), in broad concept, serves to receive the hoof for positioning and restraint, through the mediation of the boot and interface plate. In some embodiments, the system can be conceived of as two sub-assemblies: one comprising the imaging apparatus, receiving plate, and placement plate, the other comprising the hoof, hoot, and interface plate. The interface plate 'interfaces' with the placement plate to releasably attach the hoof to the imaging apparatus for imaging.

In preferred embodiments, the placement plate is a multi-strata polymer plate. At least a lowermost stratum is at least a semi-rigid polymer. At least an uppermost stratum is softer, relative to the lowermost stratum, and an attachment means is secured to the uppermost stratum for mating with the attachment means of the interface plate.

In some such preferred embodiments, the placement plate comprises two strata: an upper stratum and a lower stratum. The lower stratum is a semi-rigid polymer, providing structural integrity and support to retain the shape of the plate and to enable a mechanically secure attachment to the receiving plate. The upper stratum is a more compliant elastomeric material, providing a comfortable and skid-reducing layer for placement of the equine hoof. Molded into the upper stratum before the elastomer cures, as discussed elsewhere herein, is one side of a hook-and-loop attachment material. The hook or loop material is chosen to mate with the material of the interface plate (or vice versa-the hook-or-loop material of the interface plate is chosen to mate with the material of the placement plate). In some such embodiments, one stratum is poured in a mold, and then the second stratum is poured on top of the first stratum before it is fully cured. The hook or loop material is partially embedded into the uppermost stratum before the elastomer is fully cured, as discussed elsewhere herein in reference to the interface plate.

Figure 3:
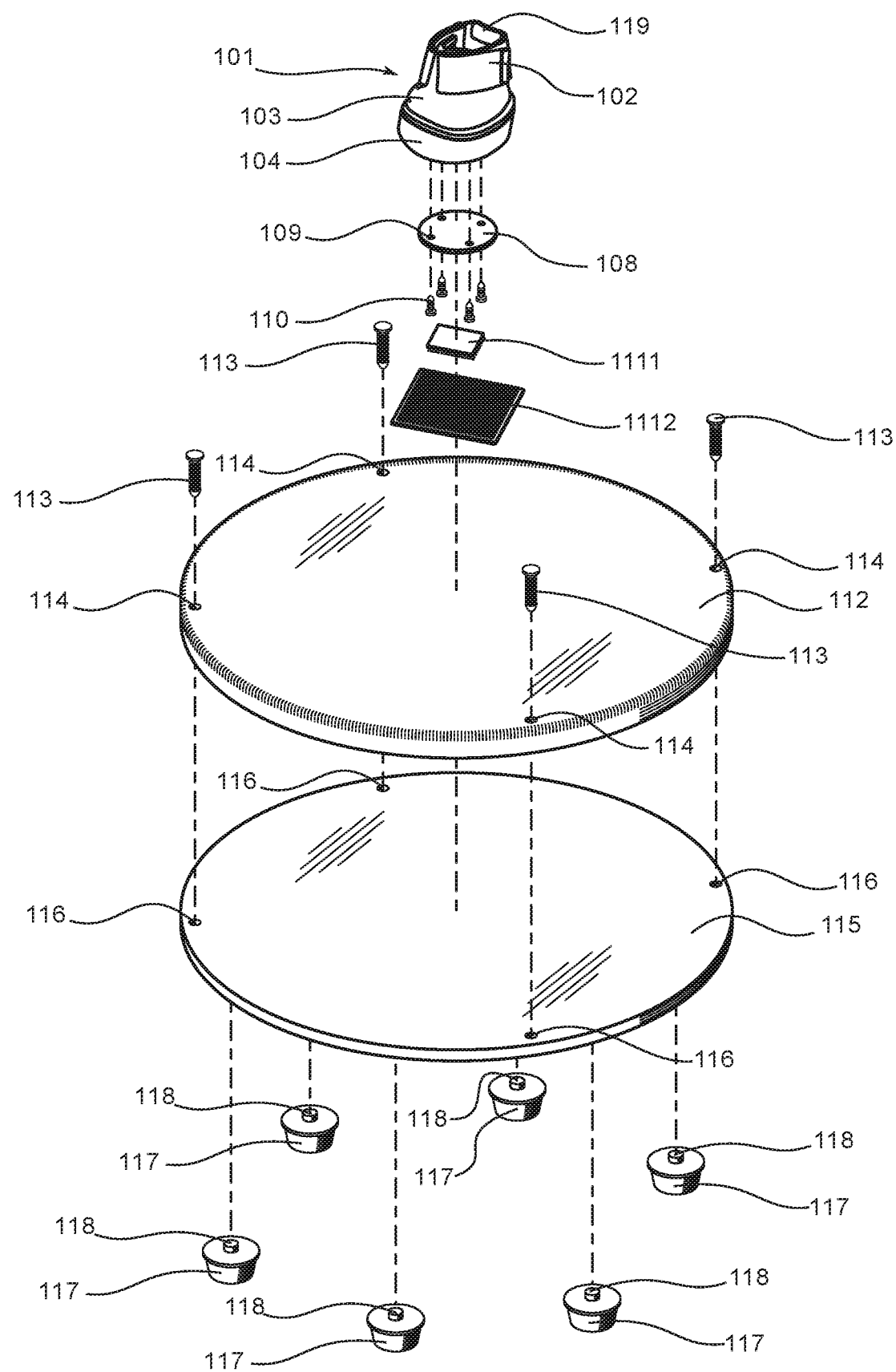
FIG. 3 is a perspective exploded view of an embodiment adapted for a NS machine.
Figure 4:
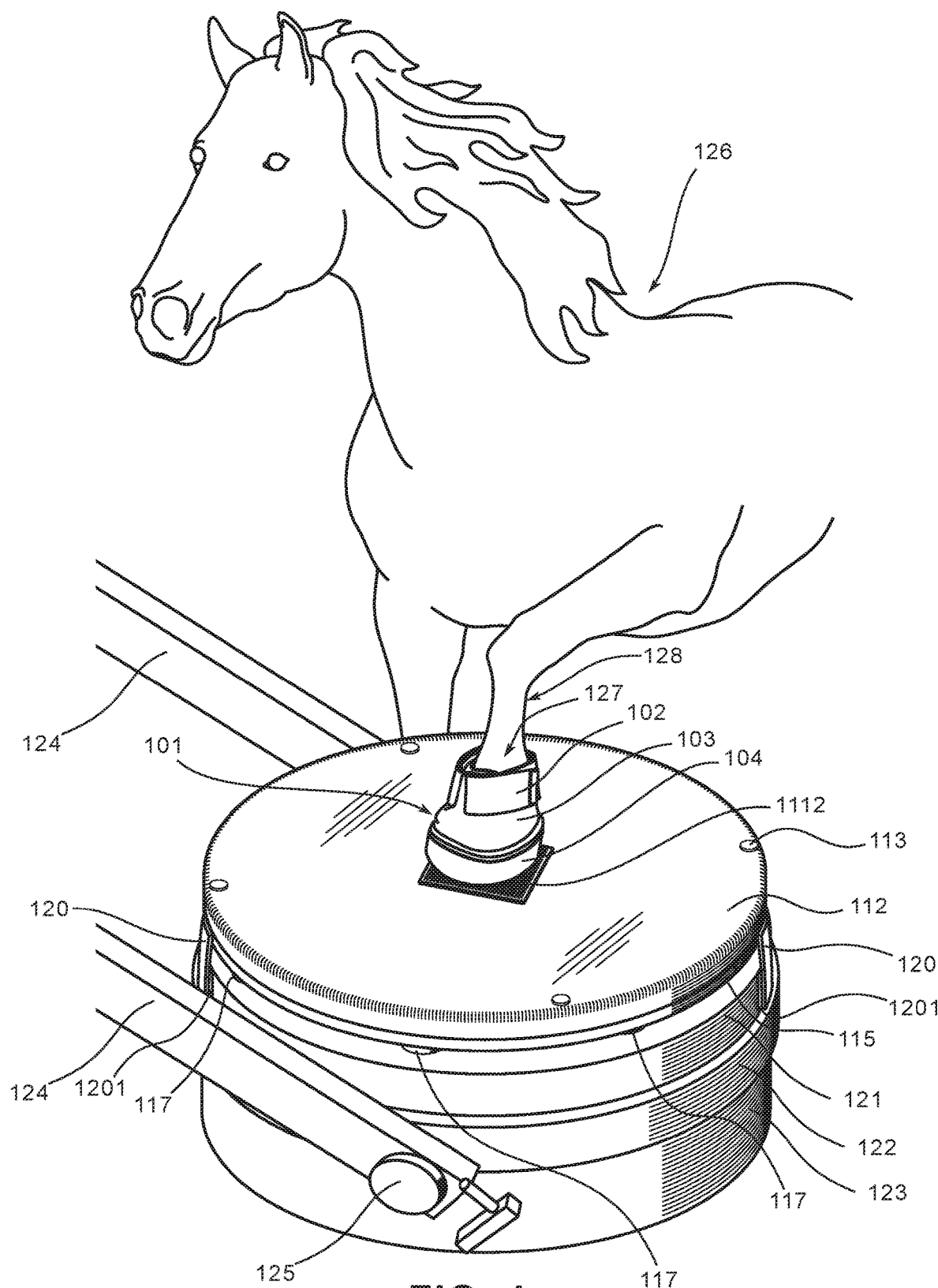
FIG. 4 is an assembled perspective view of the components shown in FIG. 3, additionally including at least part of a NS machine and showing a horse with a front left hoof positioned for imaging.
Figure 5:
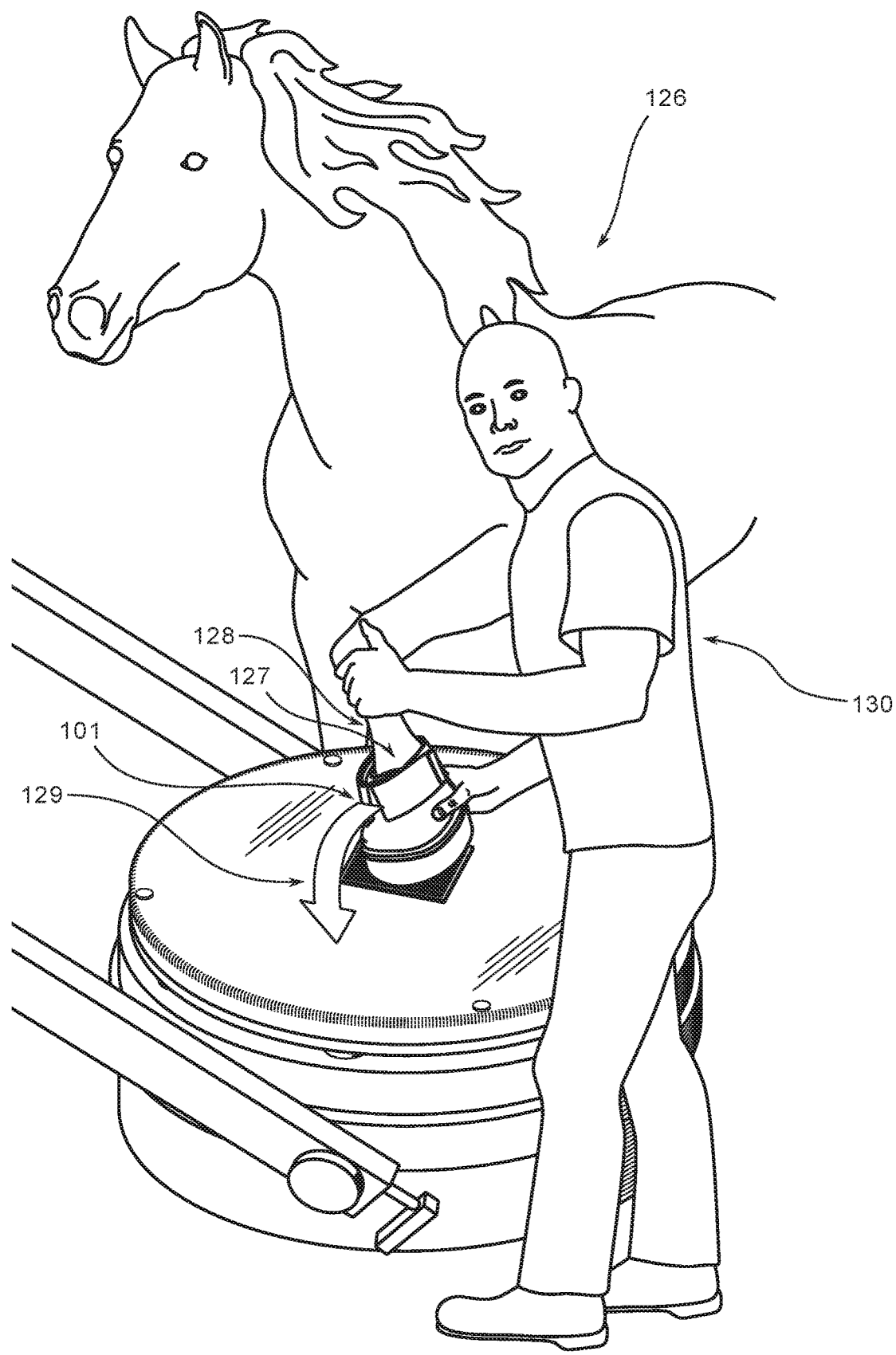
FIG. 5 is a perspective view of the assembly of FIG. 4, showing a person releasing the horse's hoof from the placement plate by rocking the hoof in the boot forward.
Figure 6:
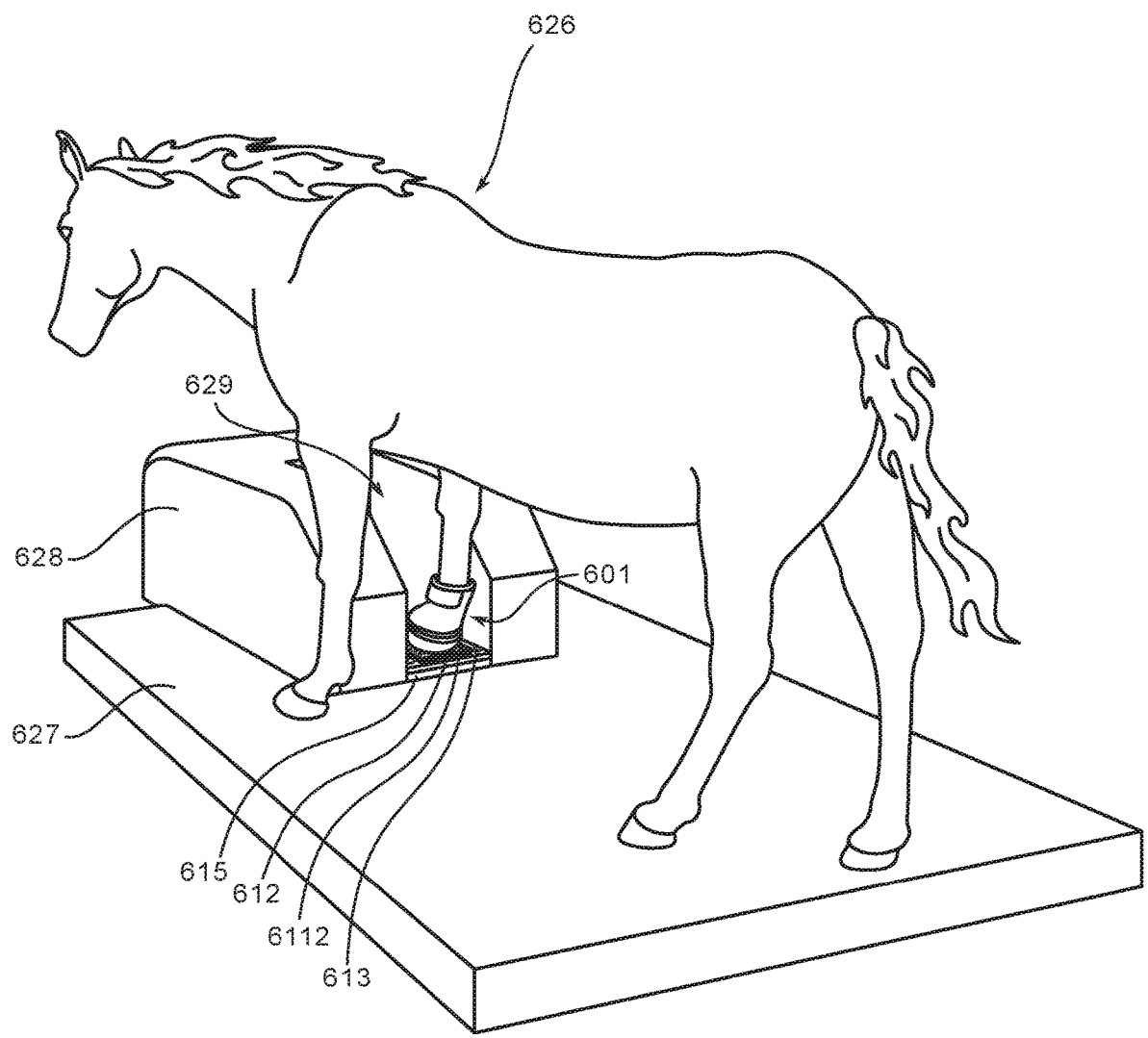
FIG. 6 is a perspective view of an embodiment adapted to an MRI machine and showing a horse with a front right hoof positioned for imaging.
Figure 7:
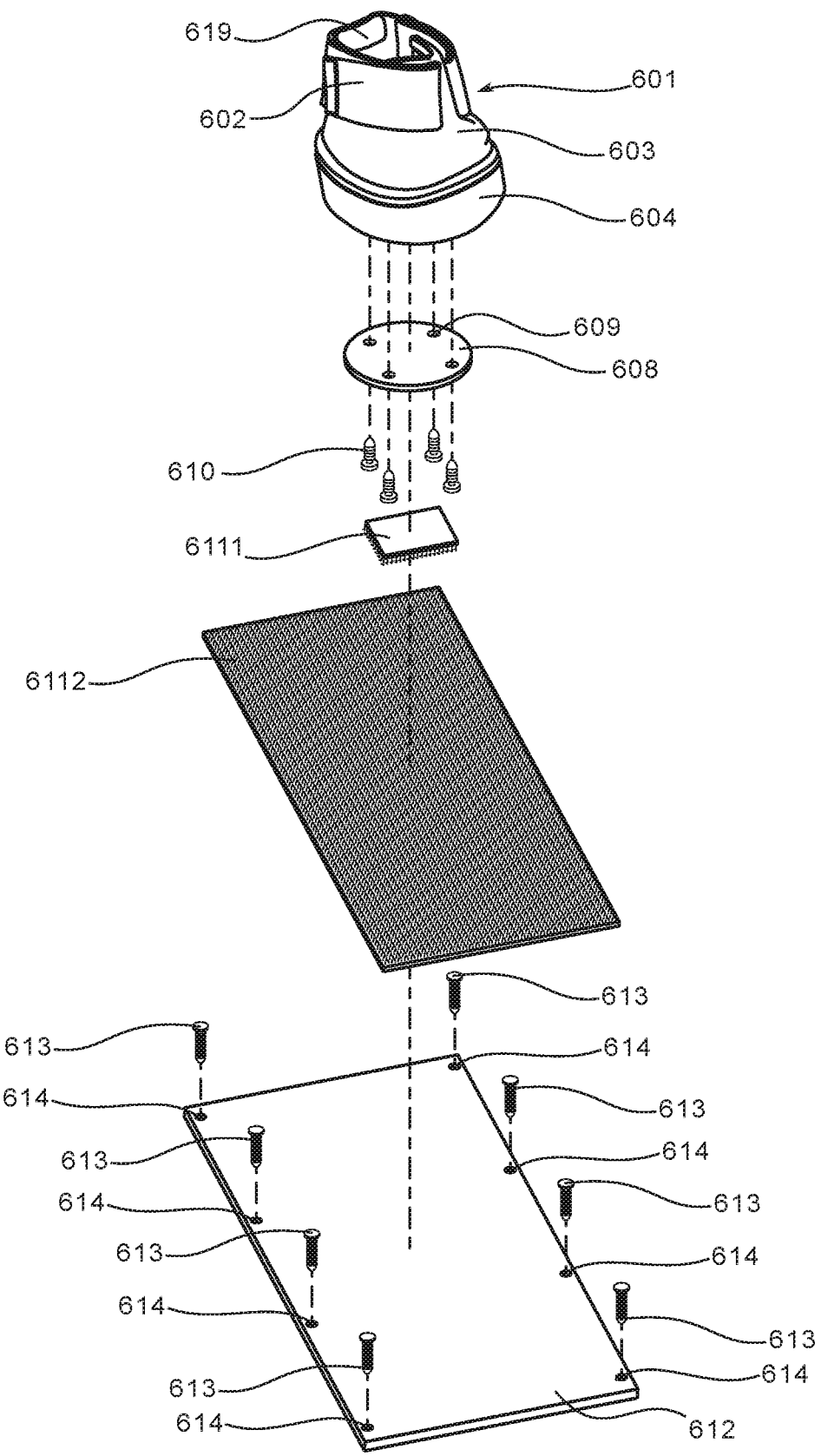
FIG. 7 is a perspective, exploded view of components included in the embodiment shown in FIG. 6.

In various embodiments, the placement plate is shaped to attach to var10us desired imaging systems, or related structures. In some embodiments for a NS imaging machine with a circular imaging plate, such as is shown in FIGS. 3-5, the placement plate (112) is a circular disc in shape and is approximately of the same diameter as the circular imaging plate (121). In some such embodiments, such as shown in FIGS. 3-5, the edges of the placement plate are radiused to promote safety and comfort. In general, the placement plate is shaped to cover the entire area over which the hoof may be placed, and is typically further provided with some amount of margin beyond that area. In various embodiments, the placement plate coordinates with, interlocks with, is incorporated into the receiving plate, the imaging apparatus, or both, or some combination thereof. In some embodiments, the placement plate is a rectangular shape (such as in FIGS. 6-7, element 612), an irregular shape, or a shape specific to a given imaging system.

In various embodiments, the placement plate is attached to the receiving plate or, in the case that the placement plate and receiving plate are a single structure, to the imaging system or appropriate substrate, by appropriate panic-releasable means. In some preferred embodiments, the placement plate is secured to the receiving plate by polymeric fir-tree type push rivets, which may be broken or pulled free by a panicked equine. In some embodiments, the rivets are recessed flush or sub-flush with the surface of the placement plate, as was discussed herein in reference to the interface plate.

In most embodiments, the force required to release the connection of the placement plate to the receiving plate is greater than the force required to disconnect the interface plate from the placement plate. In many embodiments, the force required to release the connection of the placement plate to the receiving plate is greater than the force required to release the hoof from the boot, and greater than the force required to disconnect the boot and the interface plate (which is typically greater than the force required to release the connection of the placement plate to the interface plate). Such systems are designed to maximize safety in appropriate environments by releasing the boot or hoof before releasing the plate in an attempt to avoid having the equine flailing a potentially large and dangerous structure around and, potentially, still panicking because of the attached plate. However, the attachment is still panic-releasable as a fail-safe, as releasing the placement plate is still preferable to the panicked equine still being attached to the imaging system.

In some embodiments, the placement plate is attached to the receiving plate by adhesive, by mating hook-and-loop material, by magnetic force (such as by magnets embedded in at least one of the attaching structures, and ferrous material, magnets, or both embedded in the other structure(s)), elastic material, latches, rivets, screws, bolts, locking cams, other appropriate fasteners, or various combinations thereof. In some such embodiments, the placement plate is panic-releasable from the receiving plate, as described elsewhere herein.

The Receiving Plate

In broad concept, the receiving plate serves to 'receive' the placement plate and to interface between the placement plate and the imaging apparatus. In preferred embodiments, the receiving plate is at least partially a rigid or substantially rigid structure to which is attached the placement plate, and which attaches to the imaging apparatus. In some preferred embodiments, the receiving plate is a practically rigid plate (one-eighth inch thick or thicker) made of wood (such as plywood), metal plate, aluminum plate, steel plate, polymer plate, other suitable materials and structures, and any combination thereof. In some such preferred embodiments optimized for some NS imaging machines, such as shown in FIGS. 3-5, the receiving plate (115) is a circular wooden, polymer, or metal plate between one-half to one inch thick, of the same or slightly smaller diameter than the placement plate (112). In some particular such embodiments, the underside of the receiving plate is provided with a plurality of at least partially compliant feet (117), such as out of a polymeric material, positioned around the perimeter of the underside of the receiving plate and positioned radially within one-third of the length of the radius of the receiving plate from the receiving plate's outer edge and preferably three inches from the edge. In some preferred embodiments, the feet are one-half to one and one-half inch high, and one half to four inches in diameter. In some such embodiments, there are a minimum of three, and preferably four or more such feet. In some embodiments with feet, each foot is provided with a cylindrical boss of smaller diameter than the largest diameter of the foot, such that the boss (118) fits into a matching hole (not shown) in the receiving plate (115). In various such embodiments, the foot is attached by friction, press-fitting, adhesive, threading, screw, bolt, nail, or other suitable means.

In preferred embodiments, one or more straps are provided to secure the receiving plate to the imaging apparatus. In some such preferred embodiments, such as is shown in FIG. 4, the straps are a plurality of hook-and-loop straps (120) secured to the receiving plate, by adhesive, staples, nails, screws, other suitable fasteners, or some combination thereof. In some such embodiments, one end of each strap is free such that the strap wraps around, through, etc. a structural feature on the imaging apparatus and back to the strap or to another receiving tab on the receiving plate. In other such embodiments, each strap mates with hook-and-loop material on the imaging apparatus—various embodiments have tabs on the imaging apparatus, the receiving plate, or both, some (as is shown in FIG. 4) are provided with tabs on one (120 on the receiving plate 115) and patches (1201 on the imaging head 121) on the other, some are provided with tabs and a strip, and other suitable arrangements. In some embodiments, elastic loops are provided on one plate that loop over a feature of the other plate; in some, elastic bands are provided on one plate with hooks that catch a feature of the other plate.

In some embodiments, the receiving plate attaches to the imaging apparatus, the placement plate, or both, at least partially via hook-and-loop material; in some embodiments it through magnetic force (including electromagnetic force), as discussed elsewhere herein. In some embodiments, the receiving plate attaches to the imaging apparatus, the placement plate, or both at least partially via mating surfaces, such as soft silicone, urethane, or polyurethane elastomers, that 'stick' to one another, much like a gecko's feet work. In some embodiments, attachment is by active or passive suction mechanisms, or some combination thereof. In some embodiments, a combination of attachment mechanisms are used.

The Imaging Apparatus

In broad concept, the imaging apparatus is any apparatus, assembly, or portion thereof, used for imaging. In some embodiments, the imaging apparatus may not be for imaging, but for performing another type of procedure (e.g. cancer radiotherapy, surgery, biopsy, examination, palpation, injection, etc.) on some portion of an animal, where a panic-releasable positioning and restraint system is of use, such as is discussed elsewhere herein.

In some preferred embodiments, the imaging apparatus is an x-ray, MRI, NS, or US assembly. In some such embodiments, the imaging apparatus to which the receiving plate is attached is not actually part of the imaging system itself, but an appropriate area for placement of the animal. For example, in some embodiments optimized for a standing equine MRI system, the receiving plate is attached to the floor, and the imaging apparatus comprises a scanner which at least partially surrounds the receiving plate and advances up and down vertically during imaging. In some such embodiments, and embodiments similar thereto, the 'imaging apparatus' to which the receiving plate (or other appropriate component) is attached is actually the floor (or other appropriate structure) surrounded at least partially by the scanner. More properly, this is the 'limb placement region' of the imaging apparatus. When 'imaging apparatus' is used herein to refer to attachment of the receiving plate or other components of various embodiments disclosed herein, it is used as shorthand for the 'limb placement region' of the imaging apparatus. In other words, the limb placement region is where the animal's relevant body portion is actually placed for imaging (or other relevant procedure). In many embodiments, the limb placement region and some portion of the imaging apparatus are one and the same. For example, the imaging apparatus of the NS machine provides a receiver, which the foot may be placed on. However, in another configuration, the NS receiver is placed next to the animal. Similarly, x-rays are often taken with an x-ray generator and an imaging plate, and the hoof between them, but not on them. In that case, the limb placement region is not strictly part of the imaging apparatus, but 'imaging apparatus' is often used herein, in context, and similar terms are often used in the field as shorthand for where the hoof (or other body portion) is placed.

Although preferred embodiments are directed to limbs, in various embodiments, as discussed elsewhere herein, the 'limb placement region' is actually a 'placement region' suitable not for limbs, or not only for limbs (such as legs, hooves, etc) but, in various embodiments, to other extremities (head, neck, tail, etc), to other portions of the body (barrel, ribs, hindquarters, shoulders, etc.), or combinations thereof.

In some embodiments optimized for NS, such as shown in FIGS. 4-5, the relevant portion of the imaging apparatus is a generally round cylinder (comprising cylinders 121, 122, 123), which is also the image receiver, rotatably held by two arms (124) such that one of the flat cylinder ends (the flat end of cylinder 121) remains pointed upwards. The receiving plate (115) is attached (via feet 117 and straps 120 and patches 1201) to the top of the cylinder. In some such embodiments, the imaging apparatus is not round but rectangular. In some NS embodiments, the image receiver is oriented in another direction and not configured for the equine to step on. In some such embodiments, the limb placement region is the floor, a special stand, or other suitable configuration.

In some embodiments optimized for X-ray, the limb placement region is the floor, a specialized stand, an image receiver, another suitable structure, or some combination thereof. The hoof is placed on/in the limb placement region (the hoof is in a boot, which has an interface plate on the underside) onto the placement plate, which is secured to the receiving plate Panic Release Sequence In various embodiments, various connections are panic-releasable, such as is discussed herein. In preferred embodiments, the panic-releasable connections are As discussed herein, in preferred embodiments, there are at least five panic-releasable attachments:
1) The releasable attachment of the boot onto the equine
2) The attachment of the boot to the interface plate
3) The releasable attachment of the interface plate to the placement plate
4) The attachment of the placement plate to the receiving plate
5) The attachment of the receiving plate to the imaging apparatus/limb-placement region.

All of the attachments are releasable in some embodiments—for example, by nuts and bolts, hook-and-loop, etc. In some preferred embodiments, attachments 2) and 4) are not releasable, but are still panic-releasable.

In preferred embodiments, the panic-releasable attachments release in the following order:
1) The releasable connection between the interface plate and the placement plate,
2) The releasable attachment of the boot onto the equine,
3) The attachment of the interface plate to the boot,
4) The attachment of the placement plate to the receiving plate,
5) The attachment of the receiving plate to the imaging apparatus (or other substrate.

In some preferred embodiments, connections 2) and 3) (the boot to the equine, and the interface plate to the boot, respectively) panic-release approximately simultaneously or in reverse order. In some preferred embodiments, connections 4) and 5) (the placement plate to the receiving plate, and the receiving plate to the imaging apparatus, respectively) panic-release approximately simultaneously or in reverse order.

As discussed herein, one of the primary points in the panic-release sequence is that equine (or other animal) releases from larger components in order to release the equine from components that may continue to excite panic, as well as from components that may enable the equine to do greater than normal damage (like a large placement or receiving plate)

ADDITIONAL VARIATIONS

Variations from the description above are provided in some embodiments, while retaining the nature of the invention.

Field Customization

Aspects of the interface plate, the placement plate, and boot sale are, in various embodiments, constructed of a molded elastomer which may be customized on site of use to an individual equine, machine, procedure, or individual need with standard farrier, veterinary, and other readily accessible tools such as a rasp and knives.

Patterned Plate or Pad

In various embodiments, the interface plate, the placement plate, the boot sole, or some combination thereof are patterned for purposes which include, in some embodiments, increased traction, channeling of water during washing, other purposes, and combinations thereof. Various patterns, advantageous for various applications and situations, will be understood by those of skill in the art as being within the scope of this disclosure, as described and illustrated in the examples, figures, and discussion herein.

Lightweight Construction

In some embodiments, at least one stratum of the placement plate, the interface plate, the boot sole, or any combination thereof, is made of polymer which is reduced in weight by adding low density small particles (preferably spheroidal shaped) into the polymer as is done with polymer equine boot orthotics in U.S. patent application Ser. No. 15/634,080, filed Jun. 27, 2017, U.S. patent application Ser. No. 13/396,191, filed Feb. 14, 2012, and U.S. patent Ser. No. 14/046,430 filed Oct. 4, 2013, the disclosures of which are incorporated herein by reference. The particles may be any material with sufficient flexibility and durability for incorporation into the relevant pad or plate. In a preferred embodiment wherein the polymer of the stratum is polyurethane, the particle materials are of lower density than elastomeric polyurethane, capable of being adhered to by elastomeric polymer materials (preferably polyurethane), and generally spherical or elliptical in shape. Suitable materials include, but are not limited to, polymers and elastomers, and preferably expanded foam or cellular formulation of these polymers. Specific examples include polypropylene (PP) and expanded polypropylene, polyethylene (PE) and expanded polyethylene, high density polyethylene (HDPE), ethylene propylene diene monomer (EPDM), polystyrene (PS), polyurethane (PU) and polyurethane foams, polystyrene (PS), polybutadiene, styrene-butadiene rubber (SBR), and polyvinyl chloride (PVC).

In one embodiment, PP and PE are preferred, with closed-cell expanded PP being particularly preferred for its low density, high durability, flexibility, resilience, and thermal insulation. The particle cross section or diameters are desirably in the range of one (1) to six (6) millimeters (mm) ($3.9\times10^{-1}$ to $2.4\times10^{-1}$ inches).

In a preferred embodiment, the spheroids have a diameter of approximately two (2) to four (4) mm ($7.9\times10^{-2}$ to $1.6\times10^{-1}$ inches), with approximately three (3) mm ($7.9\times10^{-2}$ inches) being particularly preferred. Particles of these sizes are small enough to be incorporated into the elastomer and large enough to not unduly increase viscosity of the polymer mixture during molding. If the particles are too large the result is a kind of permanent set reducing the flexibility and compressibility of the molded piece.

One of the key properties of the particles is their low density compared to the primary polymer of the stratum, resulting in a lower overall weight-to-volume ratio of the stratum. The difference in density between the particles and the polymer causes the particles to rise towards the top of the mold during casting, which becomes the bottom of the stratum. Because the particles are lower density than the polymer, they rise and accumulate at the top of the mold (which, in some embodiments in which the component is cast in an 'upside-down' mold, is the bottom of the stratum) during molding. The structure will then consist of one stratum comprised predominately of elastomer(s) and a bottom layer of particle-filled polymer. Such an embodiment is useful for insulation, in that the particle-filled stratum provides a thermal barrier to protect the animal from overheating. In some embodiments, the primary purpose is to reduce the overall weight of the structure (placement plate, interface plate, etc.) for ease of handling and increased safety (such as reducing personnel strain from lifting, reducing risk of injury if the structure becomes airborne, reduce the weight of the assembly on the animal, etc.) of personnel, the animal, or both.

It is obvious that in other embodiments, the relative densities of the particles and elastomer(s) may be varied to control the relative positions of elastomer and particles. The density of the particles is desirably in the range of about twenty (20) to five hundred twenty (520) grams/liter (g/l). For example, expanded polypropylene beads have a density range of about ten to two hundred (10-200) g/l, and preferred mid density beads have a density range of from about forty to one hundred twenty (40-120) g/l. Suitable PU elastomers have densities of about one thousand twenty-five to one thousand seventy (1025-1070) g/l, so the ratio of density of elastomer to particle will be in the range of from about eight to twenty-eight (8-28). It is preferred that the particles be at least half the density of the elastomer and preferably no more than about thirty (30) percent as dense.

The solid structure, if made of polymer, may be reduced in weight by adding lower density small particles into the polymer as is illustrated with polymer equine boot orthotics in the applications referenced in the introduction to the "Lite Orthotics" section.

Suitable materials may include, but are not limited to, polymers and elastomers, and preferably expanded foam or cellular formulation of these polymers. Specific examples include polypropylene (PP) and expanded PP, polyethylene (PE) and expanded PE, high density polyethylene (HDPE), ethylene propylene diene monomer (EPDM), polystyrene (PS), polyurethane (PU) and polyurethane foams, polystyrene (PS), polybutadiene, styrene-butadiene rubber (SBR), and polyvinylchloride (PVC). In one embodiment, PP and PE are preferred, with closed-cell expanded PP being particularly preferred for its low density, high durability, flexibility, resilience, and thermal insulation.

The particle cross section or diameters are desirably in the range of one (1) to six (6) millimeters (mm) ($3.9\times10^{-2}$ to $2.4\times10^{-1}$ inches). In a preferred embodiment, the particles have a diameter of approximately two (2) to four (4) mm ($7.9\times10^{-2}$ to $1.6\times10^{-1}$ inches), with approximately three (3) mm ($7.9\times10^{-2}$ inches) being particularly preferred. Particles of these sizes are small enough to be incorporated into the polymer of the structure and large enough to not unduly increase viscosity of the polymer mixture during molding. If the particles are too large the result is a kind of permanent set reducing the flexibility and compressibility of the molded piece.

In broad aspect, the method for manufacturing the lighter structure comprises mixing particles with one or more elastomer component during curing to form a molded piece. The basic process is to mix the elastomer components and catalysts, and to disperse the particles in unset polymer during curing while the polymer is still substantially in the liquid state. A mold of the desired size and shape is filled with the resulting mixture and the mixture is allowed to set and cure.

In some embodiments the structure of the shoe lower section will have fiber incorporated into it. Fibers such as those used in reinforcing cement are suitable. For example, fibers such as PP, cellulose, and carbon are suitable. Ultra-HDPE (Dyneema™ and Spectra™) are especially suitable for strength and durability. The amount of fiber in the softer stratum (or strata) of the structure must be controlled to prevent the structure from becoming too hard and the amount of fiber will depend on a number of factors, particularly the composition of the material of the structure and the hardness desired. The proper amount can easily be determined by simple experiment. Powdered Teflon™ may also be added to the structure composition to increase its strength and durability. The Teflon added to the elastomeric urethane is very abrasive resistant and is especially applicable for structures that will be repeatedly abraded during use.

Integrated Components

As referred to elsewhere herein, in various embodiments, one or more components are integrated together or into other structures. For example, in some embodiments, the receiving plate and placement plate are integrated together into substantially a single structure or assembly. In some embodiments, the interface plate and boot are integrated together into substantially a single structure or assembly, such as by embedding or attaching hook-and-loop material, part of a magnetic system, etc. to the underside of the boot sole. In some embodiments, the receiving plate is integrated into the imaging apparatus, for example, by providing holes for breakable rivets, screws, or bolts, or panic-releasable latch mechanisms for the placement plate directly to the imaging apparatus. In some such embodiments, the placement is additionally integrated into the imaging apparatus, such as by embedding or attaching hook-and-loop tape or part of a magnetic system (e.g. a magnet in the placement plate and a metal structure or reverse-oriented magnet in the interface plate, or vice versa) into the imaging apparatus.

In some embodiments, the placement plate, receiving plate, or both are integrated into a floor, stand, hoist, table, counter, wall, or other suitable structure for placement and positioning.

Kit

In some embodiments the invention is a kit of components, as that is the way in which some embodiments will be merchandised. For example, in some embodiments, a kit of replacement polymer rivets are provided for re-use of various components after a panic-release event, or removal of the interface plate from the boot for other reasons. In some embodiments, a kit comprises a boot with pre-provided holes for polymer rivets, an interface plate sized for the boot, and polymer rivets for attaching the interface plate to the hoot. In some embodiments, a kit comprises an interface plate, polymer rivets for securing it to a boot, and, in some such embodiments, a drill bit sized appropriately for making holes in the bottom of the boot. Some such embodiments further comprise plugs for plugging the holes in the bottom of the boot if the interface plate is removed.

In some embodiments, a kit comprises a placement plate, receiving plate, and rivets for attaching them together and hook-and-loop straps with adhesive or other means of attachment to the imaging apparatus. In some embodiments, a kit comprises a placement plate and rivets or other means of attachment to a receiving plate. In some embodiments, a kit comprises a hoof positioning stand (which becomes part of the imaging apparatus), a receiving plate, a placement plate, and means for attaching the various components together, as discussed elsewhere herein. In some embodiments, a kit comprises combinations of various kits or elements of kits described herein.

EXAMPLES

Example 1

In some exemplary embodiments, optimized for standing equine MRI, the boot is a Soft-Ride boot, with a plurality of holes provided in the base plate of the boot (in a preferred embodiment, four holes are provided). FIGS. 1, 2, 6, and 7 show such boots (101, 601). Measurements for at least one such suitable embodiment, constructed and tested, are provided for reference.

The interface plate (108, 608) is a single-stratum polyurethane structure, with density of Shore D sixty-five (65). Other embodiments are formed as dual-strata structure with the strata being of two different densities (and, thus, 'hardness').

The upper surface (not shown) of the interface plate is formed with a geometry complementary to the pattern (such as ridges 105 and bosses 106) on the underside of the boot's base plate, thereby allowing the interface plate to 'nestle' into the base plate (104, 604) of the boot and minimize or eliminate lateral movement of the interface plate. The interface plate is provided with matching holes (108, 608) of slightly larger diameter than the boot (to allow a rivet to pass through more easily, although in some embodiments the hole is the same or smaller diameter to further constrain lateral motion of the interface plate), and fir-tree polymer rivets (110, 610) are provided that are driven through the holes in the interface plate and into the holes (107) in the boot, which are sized to engage and retain the fins of the fir-tree polymer rivets. The interface plate is provided with a hook-and-loop material (either the hook or loop side) patch (1111, 6111) at least four (4) square inches in area, and preferably at least five to six (5-6) square inches in area, embedded in the polymer of the interface plate.

The interface plate itself is generally circular or oval in shape, and is four (4) inches wide and four and one-half (4.5) inches long (heel to toe) for a Soft-Ride® size 7L boot. For a Soft-Ride® size 5 boot, the interface plate is four and three-quarter (4.75) inches wide and five (5) inches long. Generally, the interface plate is at least three inches in diameter, or three inches across in the minor direction and is preferably no less than two inches in diameter, or two inches across m the minor direction. Preferably, the interface plate has at least some rounded or chamfered edges to minimize potentially painful or injurious corners and make the 'peeling' release motion of the boot from the placement plate easier.

The interface plate is approximately three-eighths (0.375) inch thick overall. The upper layer is of a smaller diameter to form a flange of approximately one-quarter to one (0.25-1) inch wide around the perimeter of the interface plate. The flange allows the upper layer to fit into the texture of the underside of the boot and the flange rests against the bottom of the boot, effectively increasing the surface area between the boot and the interface plate. The smaller diameter portion above the flange is approximately one-quarter (0.25) inch thick and the lower portion including the flange is approximately one-eighth (0.125) inch thick.

The hook-and-loop material embedded in the interface plate is two pieces of hook material sewn back-to-back such that both hook sides are facing outwards to form a double-sided hook material (mating to a loop material for a hook-and-loop connection system). One side of the hook material is embedded in the interface plate before it cures, leaving the other side of hook material facing outwards to mate to loop material embedded similarly in the placement plate.

The four rivets holding the interface plate into the boot have heads three-quarter (0.75) inch in diameter, stalks one-quarter (0.25) inch in diameter, and stalks three-quarter (0.75) inch in length. The rivet should be slightly shorter than the thickness of the sole, or at least than the combined thickness of the sole and the orthotic pad (if present). Suitable rivets are available from Apex Fasteners (Irwindale, Calif.), such as the PMRAR line of ratcheting action rivets (https://apexfasteners.com/fasteners/plastic-molded-products/plastic-panel-fasteners/ratcheting-action-rivets). Although intended as two-part rivets, the male portion has been found to be suitable for advantageously being used alone.

The placement plate (612) is a polyurethane single-stratum structure with density of Shore D sixty-five (65) provided with a plurality of holes (614) around the perimeter of the placement pad for use in attachment to the receiving plate (615). In some embodiments, the placement plate is a dual-strata structure.

The placement plate has a hook-and-loop material (6112) embedded into the top side. The hook-and-loop material (6112) mates with that on the interface plate (6111) (e.g. hook-side on the interface plate and loop side on the placement plate, or vice versa), the material covering an area larger than that provided on the interface plate in order to have greater freedom in placing the hoof of the horse (626). The hook-and-loop material is a double-sided material formed by taking a piece of hook material and a piece of loop material and sewing them back to back such that the hook and loop surfaces are facing outwards. The hook material is embedded in the elastomer of the placement plate before it is fully cured, leaving the loop material free and facing outwards, to mate with the hook material on the interface plate. In some embodiments, the hook material and loop material are switched such that the hook material is facing outward on the placement plate and the loop material is facing outward on the interface plate.

The placement plate is approximately twelve (12) inches square, and the hook-and-loop material is approximately seven and three-quarters (7.75) inches square. The placement plate is approximately one (1) inch thick overall. The polymer fir-tree rivets used to connect the placement plate to the receiving plate have a head of one (1) inch in diameter and a stalk three-eighths (0.375) inch in diameter and two and one-quarter (2.25) inches in length.

The receiving plate is, in some embodiments, a piece of plywood with holes (not shown) for receiving polymer fir-tree rivets (613), and with holes around the perimeter matching those in the placement plate but preferably being of a smaller diameter such that the fir-tree rivets engage the holes in the receiving plate. In preferred embodiments, there are four (4) or more holes and rivets. In some embodiments, the receiving plate has elastomeric feet, an elastomeric pad, or other suitable means, underneath the receiving plate to cushion the entire system and help provide traction, thereby reducing lateral movement. Hook-and-loop material is provided on the receiving plate that mates to hook-and-loop material on the imaging apparatus.

In some alternative embodiments, the placement plate is part of the floor (627), press-fit into a receptacle in the floor, riveted to the floor with the same fir-tree rivets (613) or other rivets, or some combination thereof.

The imaging apparatus comprises au-shaped structure (628) which contains a magnet, and which moves up and down vertically, and further comprises a floor at least inside the u-shaped structure to which the receiving plate is attached, the region inside the u-shaped structure is the limb placement region (629). The imaging apparatus also comprises a coil which is placed around the equine hoof or leg (not shown). In some such embodiments, the receiving plate and at least part of the floor of the imaging apparatus are integrated into a single structure, which is especially suitable considering that the floor must, in some variations, be raised from ground level to permit the u-shaped structure to recede flush with the floor.

Example 2

In some exemplary embodiments, illustrated in FIGS. 1, 2, 3, 4, and 5, optimized for NS of the hoof or leg, the boot, and interface plate are as in Example 1.

The placement plate (112) is a polyurethane dual-strata structure provided with a plurality of holes (114) around the perimeter of the placement pad for use in attachment to the receiving plate (115). The placement plate has a hook-and-loop material (1112) embedded into the top strata. The hook-and-loop material (1112) mates with that on the interface plate (1111) (e.g. hook-side on the interface plate and loop side on the placement plate, or vice versa), the material covering an area larger than that provided on the interface plate in order to have greater freedom in placement of the hoof (127) of the horse (126).

The receiving plate (115) is a piece of plywood with holes (116) for receiving polymer fir-tree rivets (113), and with holes around the perimeter matching the holes (114) in the placement plate, but preferably being of a smaller diameter and sized and configured for the fir-tree rivets to engage the holes (116) in the receiving plate. In preferred embodiments, there are four (4) or more holes and rivets. The receiving plate has elastomeric feet (117) secured to the underneath that cushion the entire system and help provide traction, thereby reducing lateral movement. Hook-and-loop material (120) is provided on the receiving plate that mates to hook-and-loop material on the imaging apparatus (1201).

The imaging apparatus comprises an imaging head (comprising cylinder portions 121, 122, and 123) which is a cylindrical structure which contains a receiving apparatus, and which is rotatably suspended on two arms (124, via lockable hinges 125). In some such embodiments, the hoof (127) is to be positioned on the flat top of the imaging head, when the cylinder is rotated such that the flat top is upwards and parallel with the ground. In such a case, the receiving plate is attached to the top of the cylinder.

In other such embodiments, the hoof is to be placed next to the imaging head, and the receiving plate is attached to the floor, a stand, or other appropriate structure.

Imaging Methods Using the System

Various embodiments comprise methods of positioning and restraining some portion of an equine during imaging or other procedures, as disclosed herein.

In some embodiments, a method is provided for MR imaging of an equine extremity. In some such embodiments, the method is for standing MRI of an equine hoof. For example, in some method embodiments of the system described in Example 1 herein, two boots (for both front feet) are chosen of a size to fit the equine to be imaged. If not already assembled, the interface plates (chosen of a size to fit the boots) are attached to the underside of the respective boots with the polymer rivets, by hand, with the help of a hammer, screwed-in, etc. The boots are placed on the equine's front two feet and closed with the boots' hook-and-loop closures. The imaging apparatus has already been prepared, with the receiving plate attached to the imaging apparatus, and the placement plate riveted to the receiving plate.

The equine is led up to the imaging apparatus, and a person places a booted hoof on the placement plate. The weight of the equine's hoof and leg secures the mating hook-and-loop material on the placement plate and on the interface plate together. If the hoof needs to be repositioned, as illustrated in FIG. 5, the person (130) rolls the hoof (127) forward (as shown by arrow 129), potentially by grasping both the boot (101) and the lower leg (128), initiating a 'peeling' motion that relatively easily separates the hook-and-loop materials. In some cases, the boot closure (102, as shown, for example, in FIG. 4) is opened and the hoof removed from the boot before rolling the boot forward.

In some embodiments, a method is provided for NS imaging of an equine extremity. In some such embodiments, the method is for NS of an equine hoof, leg, or both. For example, in some method embodiments of the system described in Example 2 herein, two boots (for both front feet) are chosen of a size to fit the equine to be imaged.

If not already assembled, the interface plates (chosen of a size to fit the hoots) are attached to the underside of the respective boots with the polymer rivets, by hand, with the help of a hammer, screwed-in, etc. The boots are placed on the equine's front two feet and closed with the boots' hook-and-loop closures. The imaging apparatus has already been prepared, with the receiving plate attached to the imaging apparatus, and the placement plate riveted to the receiving plate.

The equine is led up to the imaging apparatus, and a person places a booted hoof on the placement plate. The weight of the equine's hoof and leg secures the mating hook-and-loop material on the placement plate and on the interface plate together. If the hoof needs to be repositioned, the person rolls the hoof forward (in some cases, the boot closure is opened and the hoof removed from the boot before rolling the boot forward), initiating a 'peeling' motion that relatively easily separates the hook-and-loop materials.

In an embodiment in which the imaging head of the NS machine needs to be oriented pointing in parallel with the floor, the same method is followed, the only difference being that the receiving plate is not attached to the imaging head, as described elsewhere herein.

Variations of the examples and methods disclosed herein, as well as additional embodiments, are made clear to persons of ordinary skill in the art of equine imaging, veterinary medicine, and medical product design in light of the disclosure. Such variations and embodiments include, but are not limited to, imaging a rear leg instead of a front one, and imaging another body portion using an alternative 'boot' such as discussed elsewhere (a harness, collar, etc.) to position the body portion (e.g. a neck) against a placement plate in another configuration (e.g. against an imaging head of a NS machine, a wall, stocks, etc.

CONCLUSION

While the present invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept. The specification and drawings are, accordingly, to be regarded in an illustrative rather than a restrictive sense. Therefore, the scope of the invention should be limited only by the appended claims.

REFERENCES

[1] M. Winter, C. Berry, and D. Reese, "Nuclear Scintigraphy in Horses," *Compend. Cantin. Educ. Vet.*, December 2010.
[2] Wisconsin Equine Clinic, "Equine MRI (Magnetic Resonance Imaging)," *Wisconsin Equine Clinic*.
[3] S. Oke, "Standing Magnetic Resonance Imaging (MRI): Use m Diagnosing Equine Lameness." The Horse: Your Guide To Equine Health Care, 2014.
[4] T. S. Mair, J. Kinns, R. D. Jones, and N. M. Bolas, "Magnetic resonance imaging of the distal limb of the standing horse," *Equine Vet. Educ.*, vol. 17, no. 2, pp. 74-78, 2005
[5] "Gecko feet," *Wikipedia*. Published on or before 5 Feb. 2019 5 Feb. 2019. Page 28 of 31 SR-P41819.

I claim:

1. A system for use in positioning and restraining an equine hoof during imaging, said system comprising:
   a) an equine boot comprising a flexible upper section attached to a base sole, said equine boot being configured to be releasably and panic-releasably securable around an equine limb;
   b) a multi-strata interface plate being configured to be releasably and panic-releasably attached to a bottom surface of said base sole;
   c) a multi-strata placement plate being configured to be panic-releasably attached to a receiver plate and being configured to be panic-releasably attached to said interface plate; and
   d) said receiver plate being configured to be releasably and panic-releasably securable to a limb placement region of an imaging apparatus.

2. The system of claim 1, wherein said placement plate is a multi-strata polymeric plate, said multi-strata polymeric plate comprising one or more upper strata and a bottom stratum, wherein a said bottom stratum is a semi-rigid polymer that is more rigid than said one or more upper strata.

3. The system of claim 1, wherein a force required to disconnect said placement plate from said receiving plate is greater than a force required to disconnect said interface plate from said placement plate.

4. The system of claim 1, wherein a force required to disconnect said placement plate from said receiver plate is greater than a force required to disconnect an equine hoof from said equine boot, and is greater than a force required to disconnect said equine boot from said interface plate, and is greater than a force required to disconnect said placement plate from said interface plate.

5. The system of claim 1, wherein said receiver plate is attached to at least one of: said imaging apparatus and said placement plate by one of: a hook-and-loop material, a magnetic force, and an electromagnetic force.

6. The system of claim 1, wherein said interface plate is integrated into said equine boot to form a single structure.

7. The system of claim 1, wherein said interface plate and said placement plate are panic-releasably attached via hook-and-loop material and are separable by initiating a peeling motion of said interface plate with at least a pre-determined release-activation force.

8. The system of claim 1, wherein said interface plate comprises an upper stratum made of a material that is softer than a lower stratum and forms a unitary structure with strong attachment between said upper stratum and said lower stratum.

9. A system for use in positioning and restraining an equine hoof during imaging, said system being panic-releasable and comprising:
   a) an equine boot comprising a flexible upper section and a base sole, said equine boot having a releasable and panic-releasable attachment for positioning around an equine hoof;
   b) a multi-strata interface plate having a releasable and panic-releasable attachment to an underneath of said base sole;
   c) a placement plate having a panic-releasable attachment to a substantially rigid receiver plate, and having a releasable and panic-releasable attachment to said interface plate;
   d) said receiver plate having a releasable and panic-releasable attachment to a limb imaging region of an imaging apparatus;
   e) wherein said panic-releasable attachment between said interface plate and said placement plate requires the least amount of force to release than all of said panic-releasable attachments.

\* \* \* \* \*